(12) United States Patent
Mitsuhashi

(10) Patent No.: US 8,487,985 B2
(45) Date of Patent: Jul. 16, 2013

(54) IMAGING APPARATUS AND IN-VIVO IMAGE OBTAINING APPARATUS

(75) Inventor: Kei Mitsuhashi, Nishitokyo (JP)

(73) Assignee: Olympus Medical Systems Corp., Tokyo (JP)

(*) Notice: Subject to any disclaimer, the term of this patent is extended or adjusted under 35 U.S.C. 154(b) by 961 days.

(21) Appl. No.: 12/477,558

(22) Filed: Jun. 3, 2009

(65) Prior Publication Data
US 2009/0299138 A1 Dec. 3, 2009

(30) Foreign Application Priority Data

Jun. 3, 2008 (JP) ................................. 2008-146175

(51) Int. Cl.
*A62B 1/04* (2006.01)

(52) U.S. Cl.
USPC ........................................... 348/65; 348/297

(58) Field of Classification Search
USPC .................. 348/45, 51, 63, 64, 65, 67, 77, 78
See application file for complete search history.

(56) References Cited

U.S. PATENT DOCUMENTS

| | | | |
|---|---|---|---|
| 2003/0200242 A1 | 10/2003 | Jensen | |
| 2006/0170802 A1* | 8/2006 | Misawa | 348/297 |
| 2007/0126618 A1* | 6/2007 | Tanaka et al. | 341/155 |
| 2007/0252893 A1 | 11/2007 | Shigemori | |
| 2008/0100698 A1 | 5/2008 | Mori et al. | |
| 2008/0212864 A1* | 9/2008 | Bornefalk | 382/132 |

FOREIGN PATENT DOCUMENTS

| | | |
|---|---|---|
| CN | 101057490 A | 10/2007 |
| EP | 1 874 040 A2 | 1/2008 |
| JP | 02-176519 A | 7/1990 |
| JP | 2002-223390 | 8/2002 |
| JP | 2003-19111 | 1/2003 |
| JP | 2003-275171 A | 9/2003 |
| JP | 2007-208805 | 8/2007 |
| JP | 2007-251680 A | 9/2007 |
| JP | 2008-011284 A | 1/2008 |

OTHER PUBLICATIONS

European Search report dated Mar. 7, 2012 from corresponding European Patent Application No. EP 09 00 7356.0.
Chinese Office Action dated Sep. 20, 2012 in Chinese Patent Application No. 200910142166.6.
Japanese Office Action dated Nov. 13, 2012 issued in Japanese Patent Application No. 2008-146175.
European Office Action dated Apr. 9, 2013 in European Patent Application No. 09 007 356.0.

* cited by examiner

*Primary Examiner* — Barbara Burgess
(74) *Attorney, Agent, or Firm* — Scully, Scott, Murphy & Presser, P.C.

(57) ABSTRACT

An imaging apparatus includes a noise reduction circuit which eliminates a random noise generated in an analogue signal processing by equalizing, via an averaging processing, image data of correlated multiple images within one frame period which is captured by an image sensor and to which the analogue signal processing is performed in an AFE block, and the imaging apparatus in itself deals with the image data of the correlated multiple images within the one frame period and outputs the data to a wireless module after eliminating the random noise generated in the analogue signal processing.

5 Claims, 9 Drawing Sheets

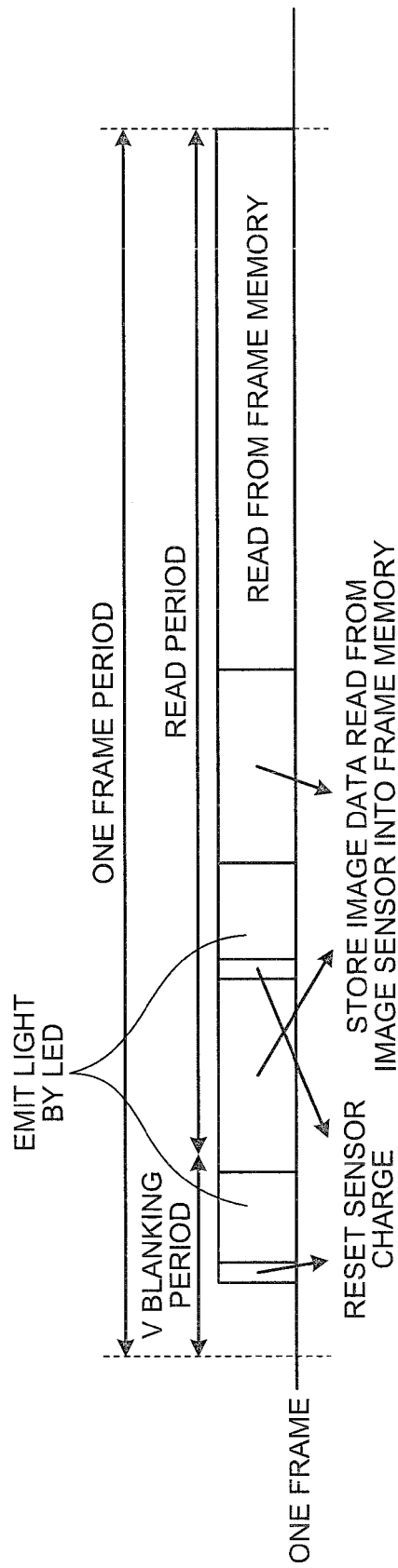

IMAGING APPARATUS AND IN-VIVO IMAGE OBTAINING APPARATUS

CROSS-REFERENCE TO RELATED APPLICATIONS

This application is based upon and claims the benefit of priority from Japanese Patent Application No. 2008-146175, filed on Jun. 3, 2008, the entire contents of which are incorporated herein by reference.

BACKGROUND OF THE INVENTION

1. Field of the Invention

The present invention relates to an imaging apparatus and an in-vivo image obtaining apparatus such as a capsule endoscope using the imaging apparatus.

2. Description of the Related Art

In recent years, a swallowable capsule endoscope which is configured by storing, in a case having a capsule shape, an imaging apparatus provided with an imaging unit that obtains image information of an inside of a subject, an illumination unit that illuminates a region to be imaged by the imaging unit, a transmitting unit that wirelessly transmits the image information obtained by the imaging unit, and the like, has been proposed and come to a stage of practical use in the field of endoscopes (see Japanese Patent Application Laid-Open No. 2003-19111, for example). Such a capsule endoscope is swallowed from a mouth of a patient as a subject and inserted into an inside of the subject. Then, the capsule endoscope, while traveling inside a body cavity according to the peristalsis, sequentially captures images of the inside of the body cavity at an interval of 0.5 second, for example, during a period until it is naturally excreted and wirelessly transmits obtained image data to a receiver placed outside the subject.

FIG. 1 is a block diagram showing an example of a schematic structure of an imaging apparatus housed in a conventional capsule endoscope. As shown in FIG. 1, the conventional imaging apparatus is constituted by: an image sensor 201 which is formed by an imaging device such as a charge coupled device (CCD) image sensor and a complementary metal oxide semiconductor (CMOS) image sensor; an analogue front-end (AFE) block 202 which performs an analogue signal processing including a gain adjustment, an analogue-to-digital (A/D) conversion, and the like with respect to image information; a digital signal processing block 203 which performs a predetermined image processing necessary with respect to the digitalized image data; a line memory 204 which stores the image data line by line; and a wireless module 205 which wirelessly outputs the image data toward a receiver and the like placed outside the subject.

Next, an example of imaging timings in a capsule endoscope provided with such an imaging apparatus is shown in FIG. 2. As shown in FIG. 2, the imaging timings are composed of: a timing of making a light source such as a light emitting diode (LED) emit light (i.e., a period for an exposure to the light); a period for reading from the image sensor 201; a period for data transmission; and blanking periods in the horizontal and the vertical directions. First by making the LED emit light during the vertical (V) blanking period of one frame period, a region to be imaged is exposed to the light and the region is captured by the image sensor 201 to obtain image information. The image information (analogue signal) which is captured and read by the image sensor 201 is digitalized as image data by undergoing a predetermined analogue signal processing in the AFE block 202, and once stored in the line memory 204 line by line after undergoing a necessary image processing in the digital signal processing block 203. Then, the image data stored in the line memory 204 is read and wirelessly output from the wireless module 205. Such operations are repeated for each line.

In addition, as shown in FIG. 3, there is another configuration which employs, instead of the line memory 204, a frame memory that can store image data for one frame and in which, after a charge accumulated in the image sensor 201 is reset, the LED is made to emit light to perform capturing by the image sensor 201, image data which is read out from the image sensor 201 and undergoes a predetermined analogue signal processing in the AFE block 202 is once stored in the frame memory frame by frame, and image data for one frame stored in the frame memory is read out to be wirelessly output from the wireless module 205.

In such an imaging apparatus, there is a case where a random noise is generated in the processing in the AFE block 202 which performs the analogue signal processing including the gain adjustment, the A/D conversion, and the like, and the noise gets on image data processed in the AFE block 202 and is wirelessly output as it is from the wireless module 205 to the outside of the body.

Such a random noise element can be balanced out and eliminated by capturing multiple images of a same frame object by the image sensor 201 through a repetition of the imaging timings shown in FIG. 2 for example, wirelessly outputting the image data processed in the AFE block 202 sequentially to the outside of the body, and performing, for example, an image averaging processing in the receiver which sequentially receives image data of these multiple images of the same frame object.

However, such a countermeasure causes deterioration in frame rate (in a case where image data of five images of the same frame object is, for example, used to perform the image averaging processing at a side of the receiver and treated as image data of one image, the frame rate deteriorates to one fifth), so that it becomes impossible to maintain a desired frame rate necessary as a capsule endoscope. Especially, since reading from the line memory which takes a substantial percentage of one frame period is repeated more than once, the frame rate easily deteriorates. To avoid the deterioration of the frame rate, it is only necessary to provide a plurality of line memories or frame memories to improve a processing speed. However, despite a demand for not increasing an amount of data to be wirelessly output and for making a size of a built-in circuit as small as possible from the view point of downsizing, low power consumption, and the like, a capsule endoscope, which is inserted into an inside of a subject and operates for a long time (eight hours, for example), goes against such a demand.

SUMMARY OF THE INVENTION

An imaging apparatus according to an aspect of the present invention includes an imaging unit which obtains image information by capturing; an analogue signal processor which performs an analogue signal processing to digitalize the image information captured by the imaging unit into image data; a digital signal processor including a noise reduction circuit that eliminates a noise generated in the analogue signal processing by equalizing image data of correlated multiple images within one frame period which is captured by the imaging unit and to which the analogue signal processing is performed in the analogue signal processor; a storage unit which updates and stores image data before and after the noise reduction performed by the noise reduction circuit; and an outputting unit which outputs the image data updated and stored in the storage unit after the noise reduction.

An in-vivo image obtaining apparatus according to another aspect of the present invention includes an imaging apparatus which includes an imaging unit which obtains image information by imaging; an analogue signal processor which performs an analogue signal processing to digitalize the image information captured by the imaging unit into image data; a digital signal processor including a noise reduction circuit that eliminates a noise generated in the analogue signal processing by equalizing image data of correlated multiple images within one frame period which is captured by the imaging unit and to which the analogue signal processing is performed in the analogue signal processor; a storage unit which updates and stores image data before and after the noise reduction performed by the noise reduction circuit; and an outputting unit which outputs the image data updated and stored in the storage unit after the noise reduction, the in-vivo image obtaining apparatus being inserted into an inside of a subject, obtaining image information of the inside of the subject by the imaging unit, and wirelessly outputting image data from the outputting unit to an outside of the subject.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 9 is a general timing chart showing an example of imaging timings of the imaging apparatus according to the third embodiment of the present invention.

DETAILED DESCRIPTION OF THE PREFERRED EMBODIMENTS

Exemplary embodiments of an imaging apparatus and an in-vivo image obtaining apparatus according to the present invention will be explained in detail below with reference to the accompanying drawings.

First Embodiment

Figure 1:
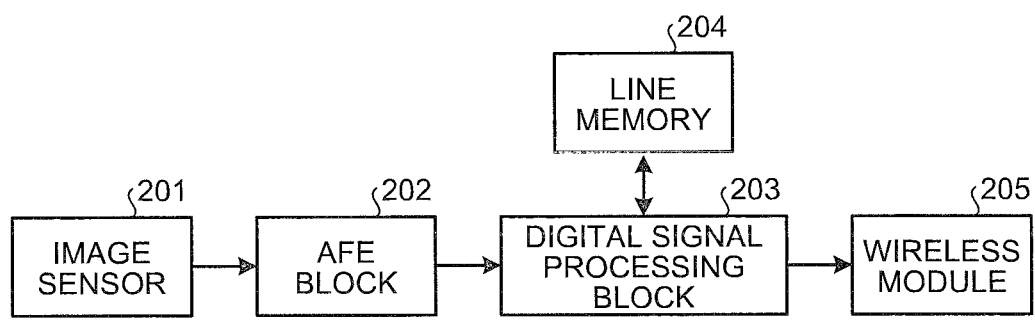
FIG. 1 is a block diagram showing an example of a schematic structure of a conventional imaging apparatus.
Figure 2:
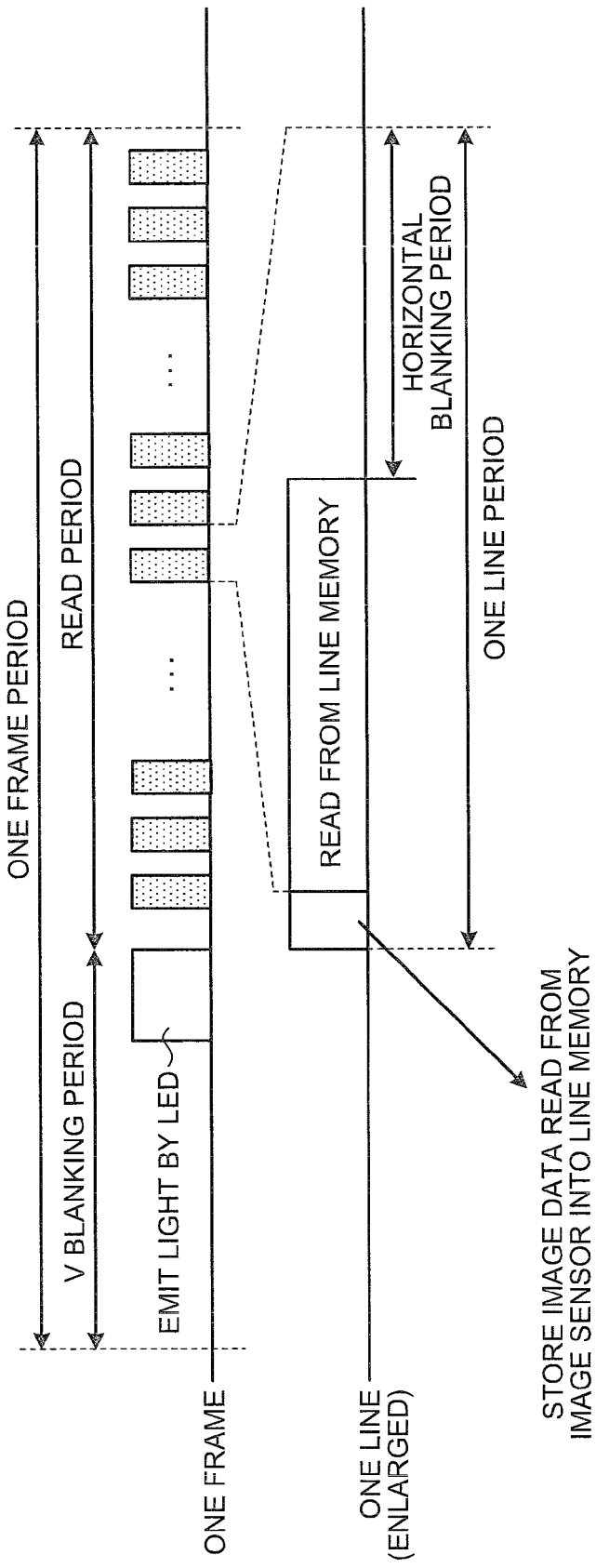
FIG. 2 is a general timing chart showing an example of conventional imaging timings.
Figure 3:
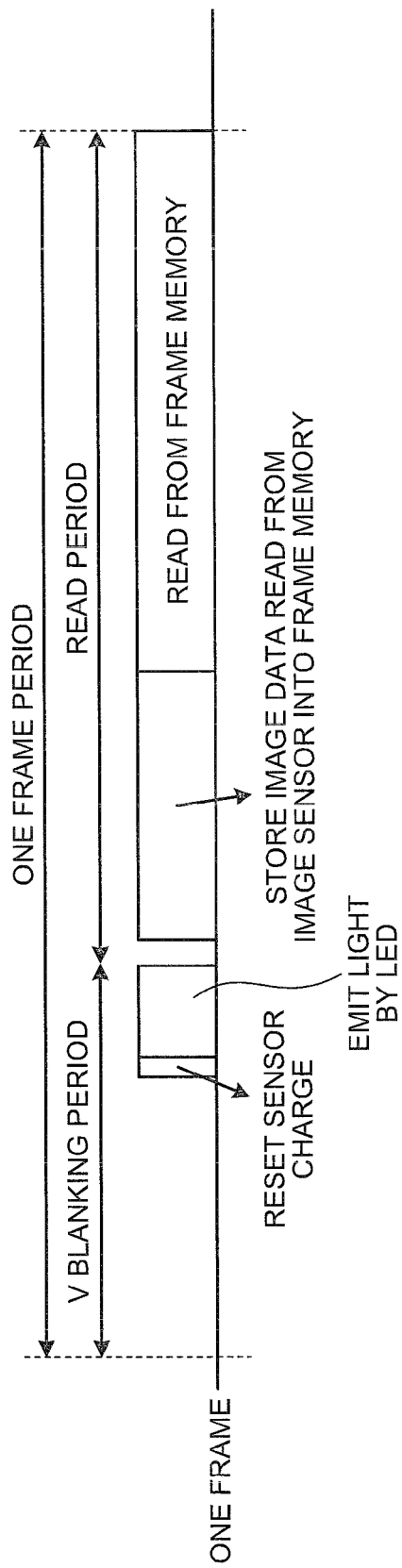
FIG. 3 is a general timing chart showing a different example of conventional imaging timings.
Figure 4:
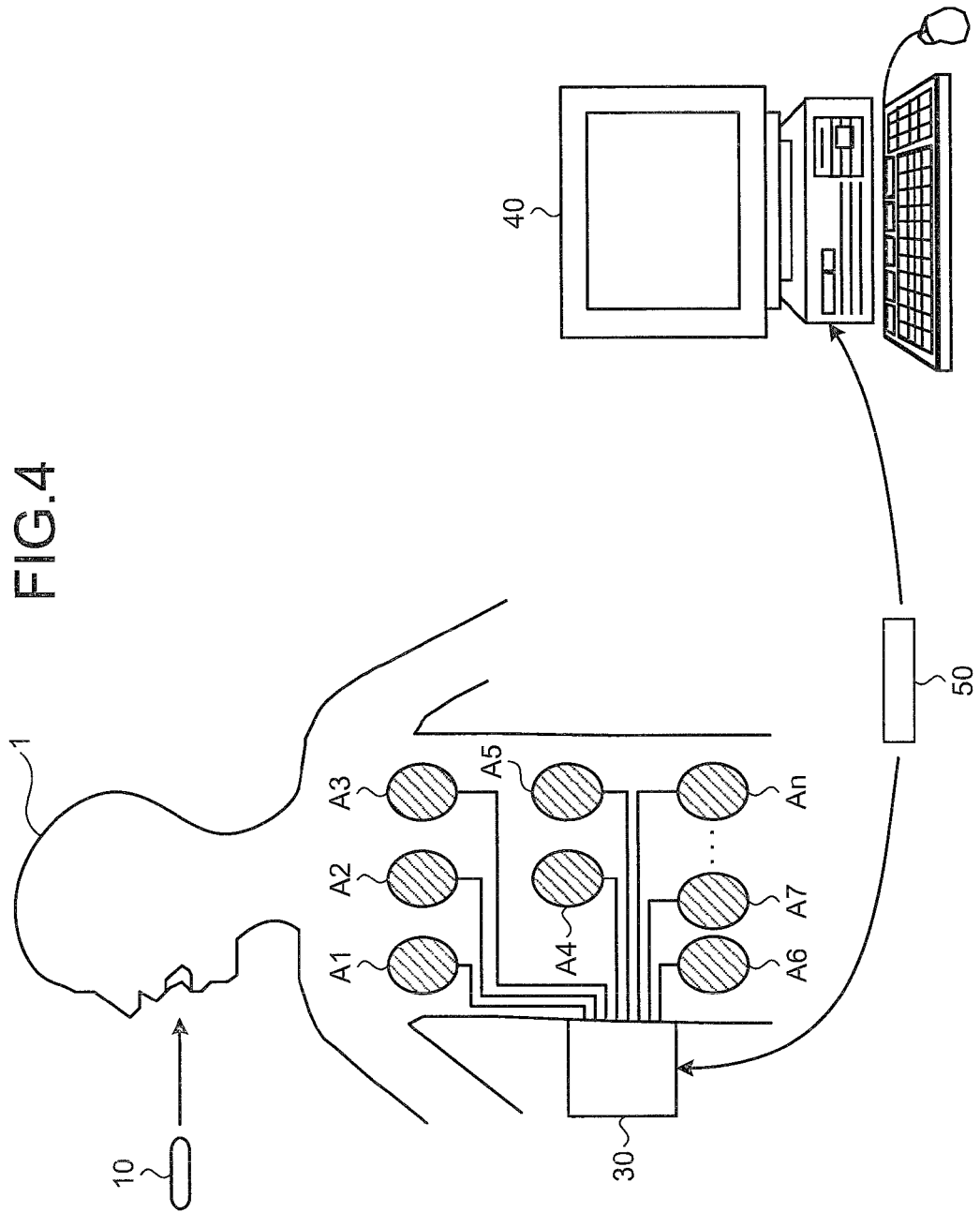
FIG. 4 is a view showing an entire structure of an in-vivo image obtaining system according to a first embodiment of the present invention.

FIG. 4 is a view showing an entire structure of an in-vivo image obtaining system according to a first embodiment of the present invention. As shown in FIG. 4, the in-vivo image obtaining system includes: a capsule endoscope 10 which is an in-vivo image obtaining apparatus that obtains image data of an inside of a subject 1; a receiver 30 which receives the image data wirelessly transmitted from the capsule endoscope 10; and a display device 40 which displays images obtained by the capsule endoscope 10 based on the image data received by the receiver 30. For a transfer of the image data between the receiver 30 and the display device 40, a portable recording medium 50 is used, for example.

The capsule endoscope 10 has an imaging function and a wireless communication function by housing an imaging apparatus inside a case which is formed in a capsule shape in a swallowable size. The capsule endoscope 10 is swallowed from a mouth of the subject 1, inserted into the inside of the subject 1, and sequentially obtains image data of an inside of a body cavity while traveling the inside of the body cavity. Then, the capsule endoscope 10 wirelessly transmits the obtained image data to the outside of the subject 1.

The receiver 30 has a plurality of receiving antennas A1 to An and receives the image data wirelessly transmitted from the capsule endoscope 10 via the respective receiving antennas A1 to An. The receiver 30 is configured such that the portable recording medium 50 as a recording medium such as CompactFlash® can be detachably attached and sequentially stores the received image data in time series in the portable recording medium 50.

The receiving antennas A1 to An are, for example, constituted by loop antennas and placed to disperse at predetermined positions on a body surface of the subject 1 as shown in FIG. 4. Specifically, the receiving antennas A1 to An are placed to disperse at positions along a traveling path of the capsule endoscope 10 inside the subject 1, for example. In addition, the receiving antennas A1 to An may be placed to disperse on a jacket to be worn by the subject 1. In this case, when the subject 1 wears the jacket, the receiving antennas A1 to An are placed to disperse at predetermined positions on the body surface of the subject 1 along the traveling path of the capsule endoscope 10 inside the subject 1. Here, the number of antennas is not specifically limited as long as at least one antenna is placed with respect to the subject 1.

The display device 40 is realized by a workstation or a general-purpose computer such as a personal computer, and is configured such that the portable recording medium 50 can be detachably attached. The display device 40 reads the image data stored in the portable recording medium 50 and displays the read image data on a display device such as a liquid crystal display (LCD) device and an electroluminescent display (ELD) device. Besides, the display device 40 arbitrarily allows writing information of the subject 1 into the portable recording medium 50. Here, the display device 40 may also be configured to output the image data to another medium such as a printer.

Figure 5:
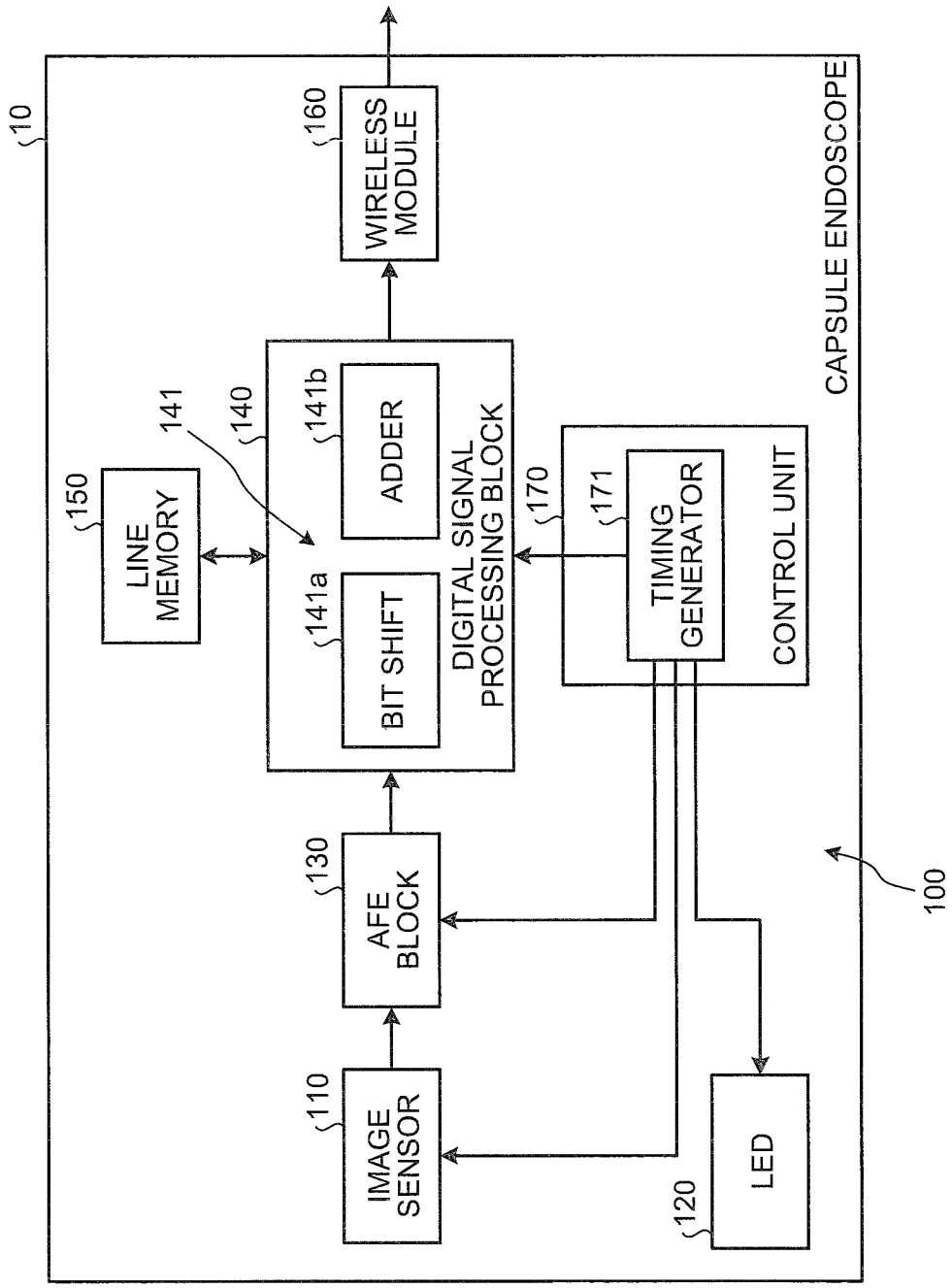
FIG. 5 is a block diagram showing an example of a schematic structure of an imaging apparatus housed in a capsule endoscope according to the first embodiment of the present invention.

Next, a structure of the imaging apparatus which is housed in the capsule endoscope 10 according to the first embodiment and realizes the imaging function and the wireless function will be explained. FIG. 5 is a block diagram showing an example of a schematic structure of an imaging apparatus 100 housed in the capsule endoscope 10. As shown in FIG. 5, the imaging apparatus 100 includes an image sensor 110, an LED 120, an analogue front-end (AFE) block 130, a digital signal processing block 140, a line memory 150, a wireless module 160, and a control unit 170.

The image sensor 110 constitutes an imaging unit and the CMOS image sensor is, for example, used in the first embodiment. The image sensor 110 performs an imaging operation of capturing an image of an imaging region inside the subject 1 by outputting, after incident light from the imaging region is focused by an imaging optical system such as an imaging lens, an analogue signal according to an intensity of the incident light as image information. The timing of the imaging operation performed by the imaging sensor 110, and the timing and the number of an operation of reading out the analogue signal from the image sensor 110 are controlled according to a timing signal given from a timing generator 171.

The LED 120 is provided as one example of a light source which illuminates an imaging region, and by being driven to emit light by an LED driving circuit, irradiates and illuminates with illumination light the region to be imaged by the image sensor 110. The timing of the light emitting operation of the LED 120 is controlled according to the timing signal from the timing generator 171.

The AFE block 130 functions as an analogue signal processor, performs an analogue signal processing such as a gain adjustment (including a correlated double sampling, amplification, and the like) and an analogue-to-digital (A/D) conversion with respect to the analogue signal (image information) captured by and output from the image sensor 110, and outputs the digitalized image data.

The digital signal processing block 140 functions as a digital signal processor, reads out, after performing a predetermined image processing such as a white balance, a γ correction, and a color correction with respect to the image data digitalized by the AFE block 130 and storing the data once into the line memory 150, the image data from the line memory 150 according to a readout timing, and outputs the data to the wireless module 160. Here, the digital signal processing block 140 in the first embodiment includes a noise reduction circuit 141. The noise reduction circuit 141 serves to reduce a random noise which is generated with the analogue signal processing performed by the AFE block 130, and is constituted by a bit shift circuit 141a and an adder 141b in the first embodiment. The bit shift circuit 141a does a division by shifting image data per pixel to right by predetermined number of bits "n", for example, n=2. The adder 141b uses the line memory 150 to perform a processing of adding image data per pixel.

The wireless module 160 is constituted by: a transmitting circuit which performs a data processing such as a modulation processing with respect to the image data read out by the digital signal processing block 140 from the line memory 150 to generate a wireless signal; an antenna for transmitting the generated wireless signal to the outside; and the like, and wirelessly transmits image data to the outside.

The control unit 170 controls each unit constituting the imaging apparatus 100 and controls operations of the entirety of the imaging apparatus 100 as a whole. The control unit 170 includes the timing generator 171 which generates and outputs a timing signal for controlling an operation timing with respect to each unit.

Figure 6:
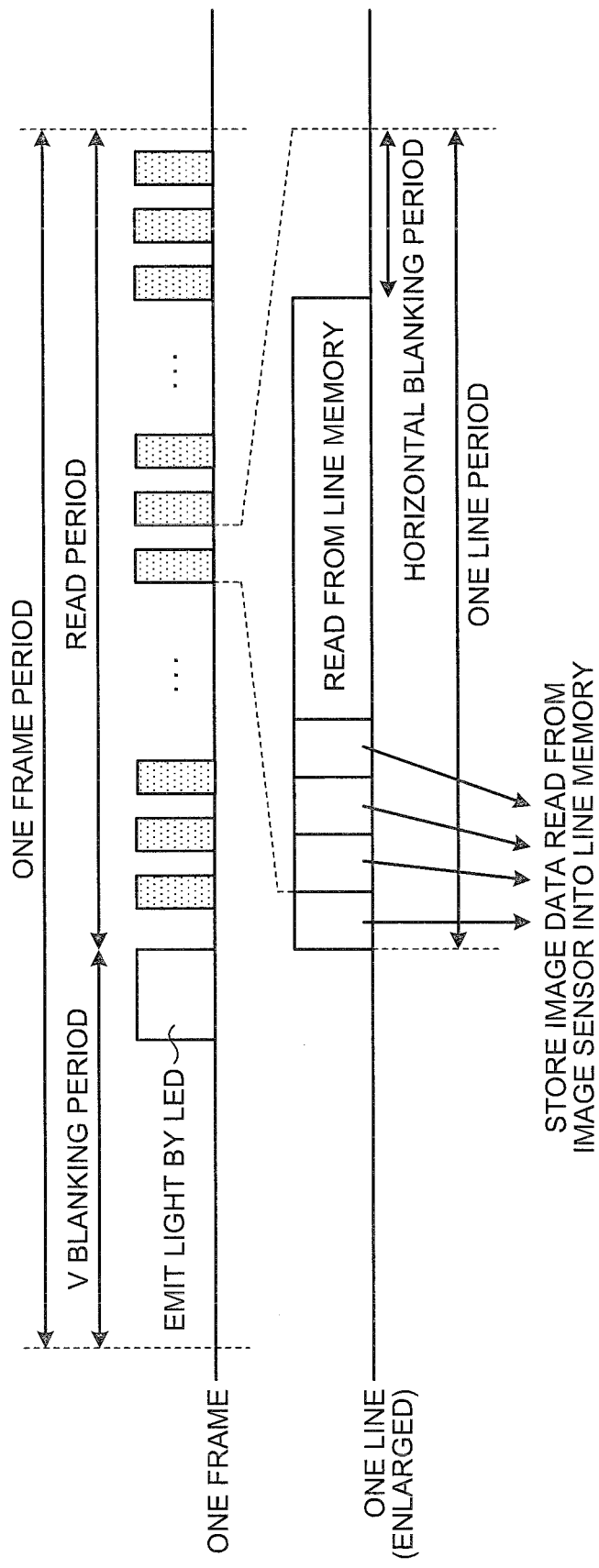
FIG. 6 is a general timing chart showing an example of imaging timings of the imaging apparatus according to the first embodiment of the present invention.

In such a configuration, an example of controlling the operation of the imaging apparatus 100 housed in the capsule endoscope 10 will be explained. FIG. 6 is a general timing chart showing an example of imaging timings of the imaging apparatus 100. In the first embodiment, a random noise is controlled to be reduced by reading out as image data of correlated multiple images within one frame period, more than once, for example repetitively four times in succession, same image information which is captured by the image sensor 110 realized by the CMOS image sensor and stored until a charge reset and by calculating an average value for each pixel by the noise reduction circuit 141 and the line memory 150 after the analogue signal processing performed by the AFE block 130.

First, image information is read out from the image sensor 110 line by line and undergoes necessary analogue signal processing in the AFE block 130. With respect to the image data digitalized by the AFE block 130 in the digital signal processing block 140, the bit shift circuit 141a is first used to do a division into one fourth by a processing of shifting to right by two bits per pixel. One line image data after the bit shifting is once stored in the line memory 150. Next, image information of the same line (same image information) kept in the image sensor 110 is read out, and the analogue signal processing and the two-bit right shifting processing are similarly performed respectively in the AFE block 130 and the bit shift circuit 141a. Then, the adder 141b is used to add one line image data after the latter bit shifting to one line image data which is stored in the line memory 150 after the former bit shifting and an addition result is updated and stored in the line memory 150. Such a processing is repeated additionally twice and performed four times in total, so that an average of values corresponding to the four times for each pixel with respect to image data based on the same image information is updated and stored in the line memory 150. Here, the image data for the four times based on the same image information is essentially supposed to be exactly the same and a random noise element generated due to the analogue signal processing in the AFE block 130 is balanced out, eliminated, and equalized by calculating the average value of the image data for the four times. In this manner, one line image data in which a random noise caused by the AFE block 130 is equalized is updated and stored in the line memory 150. Then, image data is wirelessly output from the wireless module 160 line by line by reading out the one line image data updated and stored in the line memory 150 after the fourth processing.

According to the first embodiment as described, since the noise reduction circuit 141 which eliminates a random noise generated in the analogue signal processing by equalizing, via the averaging processing, same image data in a unit of multiple images (four images, four example) within one frame period which is captured by the image sensor 110 and to which the analogue signal processing is performed in the AFE block 130 is provided, and since the imaging apparatus 100 in itself deals with the same image data of the unit of multiple images within one frame period and outputs the data to the wireless module 160 after eliminating a random noise generated in the analogue signal processing, an influence of a random noise generated due to the analogue signal processing can be reduced without degrading a frame rate. Specifically, since, in addition to the fact that the light emission of the LED 120 is needed only once, the processing of reading out the same image information from the image sensor 110 and the processing of storing the data into the line memory 150 can be completed substantially in shorter time period than the processing of reading out image data from the line memory 150, the repetition of reading out more than once the same image information within one line period hardly affects a frame rate.

Besides, as the averaging processing performed by the noise reduction circuit 141, image data may be sequentially added first for each pixel by the adder 141b, then updated and stored in the line memory 150, and finally divided via the bit shifting in the bit shift circuit 141a. In the first place, since an ultimate image data amount is configured to be as much as one line, not by storing entire image data for each pixel in the line memory 150 in taking the average as described above but by sequentially adding and storing image data in the line memory 150 after dividing image data for each pixel via the bit shifting, it is only necessary in the first embodiment to prepare a storage capacity for one line of image data corresponding to a normal one image and thereby also possible to avoid a growth in size of a circuit. Consequently, the configuration in the first embodiment comes to match the demand for not increasing an amount of data to be wirelessly output and for making a size of a built-in circuit as small as possible, which is expected for the capsule endoscope 10, from the view point of downsizing, low power consumption, and the like.

In addition, as the averaging processing in the noise reduction circuit 141, only the adding processing performed by the adder 141*b* more than once may be executed and the addition result may be treated as the average value, without using the bit shift circuit 141*a*.

Second Embodiment

Figure 7:
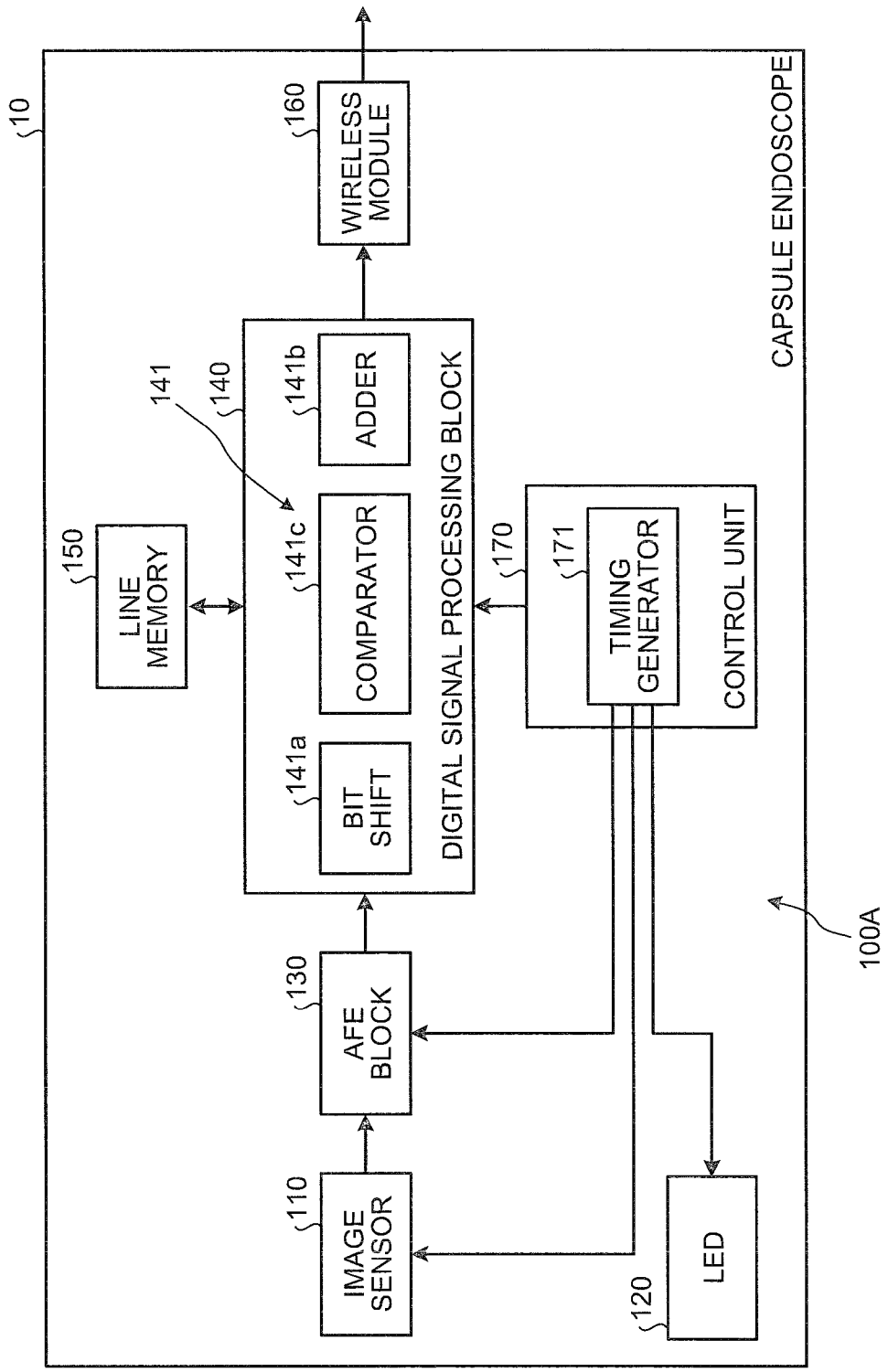
FIG. 7 is a block diagram showing an example of a schematic structure of an imaging apparatus housed in a capsule endoscope according to a second embodiment of the present invention.

Next, an imaging apparatus and a capsule endoscope according to a second embodiment of the present invention will be explained. FIG. 7 is a block diagram showing an example of a schematic structure of an imaging apparatus 100A housed in the capsule endoscope 10 according to the second embodiment. In the imaging apparatus 100A according to the second embodiment, a random noise is controlled to be reduced in such a configuration that the noise reduction circuit 141 includes a comparator 141*c* in addition to the bit shift circuit 141*a* and the adder 141*b*, and performs an averaging processing by using the comparator 141*c* to calculate intermediate values obtained after eliminating a maximum value and a minimum value for each pixel of image data and calculate an average value of the intermediate values.

Similarly to the case shown in FIG. 6, for example, same image information which is captured by the image sensor 110 realized by the CMOS image sensor and is stored until a charge reset is read out as image data of correlated multiple images, more than once, for example four times in succession. In this case, the bit shift circuit 141*a* is used to do a division into one second by performing a one-bit right shifting processing per pixel in the first processing. Then, one line image data after the bit shifting is once registered in the comparator 141*c* for each pixel as a maximum value and a minimum value for comparison. Next, the bit shift circuit 141*a* is used to do the division into one second by performing the one-bit right shifting processing per pixel in the second processing. Then, one line image data after the bit shifting is compared with the maximum value and the minimum value registered in the comparator 141*c* for each pixel. When the latest one line image data after the bit shifting is smaller than the maximum value and larger than the minimum value, the one line image data is extracted as an intermediate value, undergoes an adding processing performed by the adder 141*b*, and is once stored in the line memory 150.

On the other hand, when the latest one line image data for each pixel after the bit shifting is larger than the maximum value or smaller than the minimum value, the latest image data is newly registered as a maximum value or a minimum value at the pixel, and is not transmitted to the adder 141*b*. Such a processing is repeated additionally twice, so that the adder 141*b* performs an adding processing of intermediate values, corresponding to the two times, which are obtained after eliminating the maximum value and the minimum value and can calculate an average value between the intermediate values.

Therefore, though it is necessary to add the comparator 141*c* according to the second embodiment, since image data is equalized by calculating an average value between intermediate values after eliminating a maximum value and a minimum value, a random noise generated in the AFE block 130 can further easily be reduced.

It should be noted that though the noise reduction circuit 141 according to the second embodiment is configured to calculate an average value between intermediate values by including the bit shift circuit 141*a* and the adder 141*b* in addition to the comparator 141*c*, and repeating the processing based on same image information four times, the processing based on same image information may be repeated, for example, three times and image data corresponding to an intermediate value extracted by the comparator 141*c* may be dealt with as it is.

Third Embodiment

Figure 8:
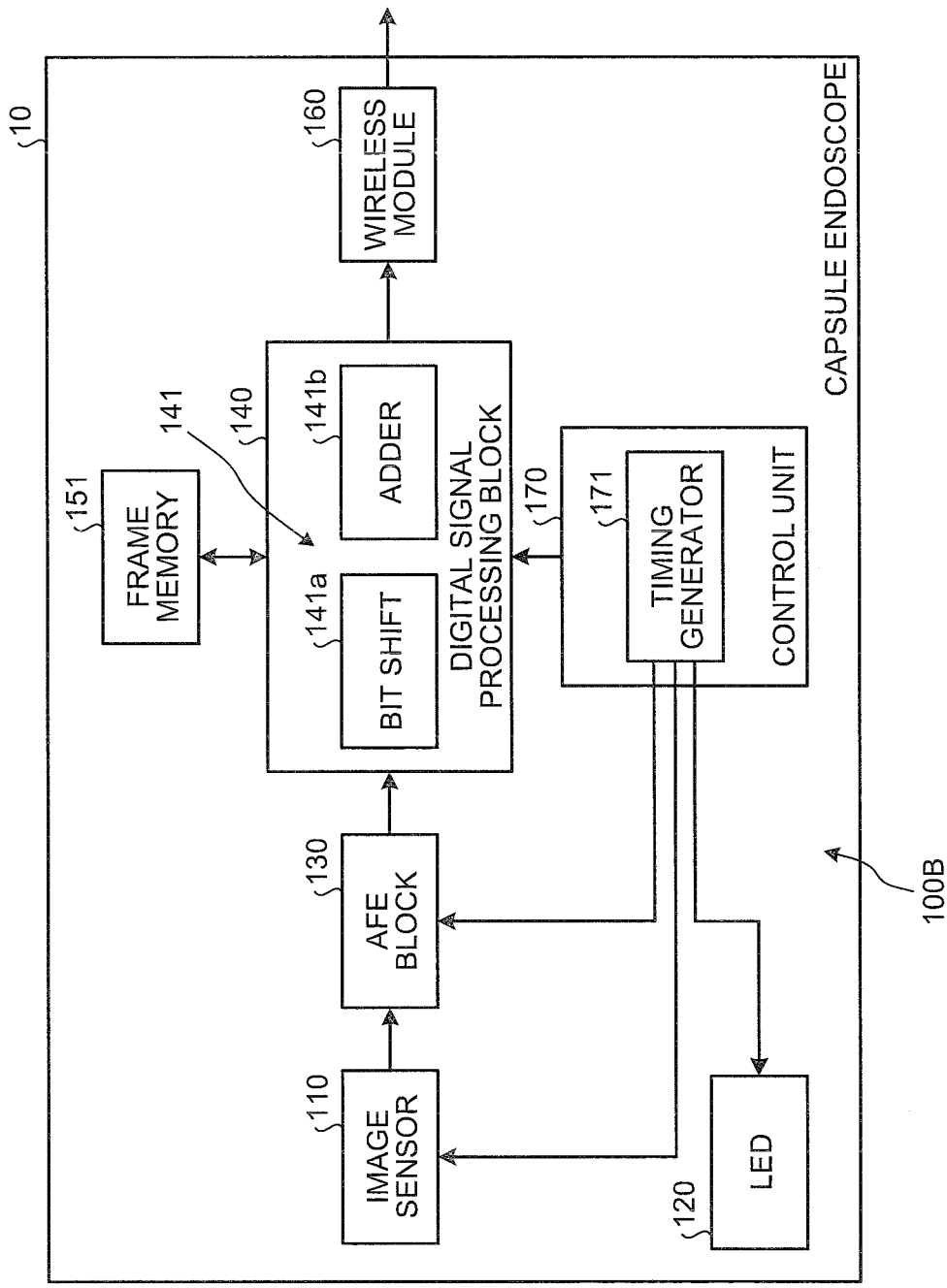
FIG. 8 is a block diagram showing an example of a schematic structure of an imaging apparatus housed in a capsule endoscope according to a third embodiment of the present invention.

Next, an imaging apparatus and a capsule endoscope according to a third embodiment of the present invention will be explained. FIG. 8 is a block diagram showing an example of a schematic structure of an imaging apparatus 100B housed in the capsule endoscope 10 according to the third embodiment and FIG. 9 is a general timing chart showing an example of imaging timings of the imaging apparatus 100B. The imaging apparatus 100B according to the third embodiment is configured to perform a processing in a unit of a frame by including a frame memory 151 as a storage unit instead of the line memory 150. Besides, same image information of multiple images itself is not used as image data of correlated multiple images within one frame period, and image information of multiple images, for example two images, which are obtained by imaging same region more than once, for example twice in succession within one frame period by the image sensor 110 and can be regarded as same images is used in the third embodiment. Then, a random noise is controlled to be reduced by sequentially reading out image information for two images captured in succession and calculating an average value for each pixel by the noise reduction circuit 141 and the frame memory 151 after the analogue signal processing performed by the AFE block 130.

First, an imaging is performed by the image sensor 110 by making the LED 120 emit light after a sensor charge reset. Then, image information is read out from the image sensor 110 frame by frame and undergoes necessary analogue signal processing in the AFE block 130. With respect to the image data digitalized by the AFE block 130 in the digital signal processing block 140, the bit shift circuit 141*a* is used to do a division into one second by a one-bit right shifting processing for each pixel. One frame image data after the bit shifting is once stored in the frame memory 151. Next, a second imaging is performed in succession by the image sensor 110 by making the LED 120 emit light after a sensor charge reset. Then, image information is read out from the image sensor 110 frame by frame and undergoes necessary analogue signal processing in the AFE block 130. With respect to the image data digitalized by the AFE block 130, the bit shift circuit 141*a* is used to do the division into one second by the one-bit right shifting processing for each pixel. Then, the adder 141*b* is used to add one frame image data after the latter bit shifting to the one frame image data which is stored in the frame memory 151 after the former bit shifting and an addition result is updated and stored in the frame memory 151. By performing such a processing, an average of values corresponding to the two times for each pixel with respect to image data based on the image information equivalent to same image information captured in succession is updated and stored in the frame memory 151. In this manner, one frame image data in which a random noise due to the AFE block 130 is equalized is updated and stored in the frame memory 151. Then, image data is wirelessly output from the wireless module 160 frame by frame by reading out the one frame image data updated and stored in the frame memory 151 after the second processing.

According to the third embodiment as described, since the noise reduction circuit 141 which eliminates a random noise generated in the analogue signal processing by equalizing, via the averaging processing, successively captured image data equivalent to same image data of multiple images (two images, for example) within one frame period which is captured by the image sensor 110 and to which the analogue signal processing is performed in the AFE block 130 is provided, and since the imaging apparatus 100B in itself deals with the successively captured image data equivalent to the same image data of multiple images within one frame period and outputs the data to the wireless module 160 after eliminating a random noise generated in the analogue signal processing, an influence of a random noise generated due to the analogue signal processing can be reduced without degrading a frame rate. Specifically, since the processing of reading out image information more than once from the image sensor 110 and the processing of storing the data into the frame memory 151 can be completed substantially in shorter time period than the processing of reading out image data from the frame memory 151, the repetition of reading out more than once image information within one frame period hardly affects a frame rate.

Besides, as the averaging processing performed by the noise reduction circuit 141, image data may be sequentially added for each pixel by the adder 141b first, then updated and stored in the frame memory 151, and finally divided via the bit shifting by the bit shift circuit 141a. In the first place, since an ultimate image data amount is configured to be as much as one frame, not by storing entire image data for each pixel in the frame memory 151 in taking the average as described above but by sequentially adding and storing image data in the frame memory 151 after dividing image data for each pixel via the bit shifting, it is only necessary to prepare, as a capacity of the frame memory 151, a storage capacity for image data of a normal one frame and thereby also possible to avoid a growth in size of a circuit.

As the averaging processing in the noise reduction circuit 141, only the adding processing performed by the adder 141b more than once may be executed and the addition result may be treated as the average value, without using the bit shift circuit 141a.

In addition, though the line memory 150 or the frame memory 151 is provided and image data is input and output line by line or frame by frame in the embodiments described above, a memory for a unit of a pixel which is a minimum unit may be employed and image data may be input and output pixel by pixel.

Besides, as the image sensor 110, not only the CMOS image sensor but also an imaging element such as the CCD may be used. In the case of using the CCD, it is only necessary that an imaging is performed more than once in succession within one frame period and image data of correlated multiple images which can be regarded as same image information is dealt with, as shown in the third embodiment, for example.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An in-vivo image obtaining apparatus comprising:
   an imaging unit which obtains in-vivo image information by imaging;
   an analogue signal processor which performs an analogue signal processing to digitalize the image information captured by the imaging unit into image data;
   a digital signal processor which processes the signal from the analogue signal processor, the digital signal processor including a noise reduction circuit that eliminates a noise generated in the analogue signal processing by equalizing image data of correlated multiple images within one frame period which is captured by the imaging unit and to which the analogue signal processing is performed in the analogue signal processor, the noise reduction circuit including an adder, a bit shift circuit and a comparator, wherein:
   the adder sequentially adds the image data of correlated multiple images for each pixel for the equalization,
   the bit shift circuit performs a bit shifting on image data for each pixel,
   the adder adds one of image data before and after the bit shifting performed by the bit shift circuit for each pixel and calculates an average value for each pixel of the image data of correlated multiple images for the equalization, and
   the comparator eliminates a maximum value and a minimum value for each pixel from the image data of correlated multiple images, and extracts an intermediate value which is obtained after eliminating the maximum value and the minimum value for each pixel for the equalization;
   a storage unit which updates and stores image data before and after the noise reduction performed by the noise reduction circuit; and
   a wireless module which processes the signal from the digital signal processor and outputs the image data updated and stored in the storage unit after the noise reduction.

2. The in-vivo image obtaining apparatus according to claim 1, wherein the image data of correlated multiple images within the one frame period is image data based on same image information which is repetitively read out as multiple images from the imaging unit within the one frame period.

3. The in-vivo image obtaining apparatus according to claim 1, wherein the image data of correlated multiple images within the one frame period is image data based on image information which is imaged in succession by the imaging unit as multiple images and sequentially read out from the imaging unit within the one frame period.

4. The in-vivo image obtaining apparatus according to claim 1, wherein the noise reduction circuit inputs and outputs the image data of correlated multiple images in one of a pixel unit, a line unit, and a frame unit.

5. The in-vivo image obtaining apparatus according to claim 4, wherein the storage unit is one of a pixel unit memory, a line unit memory, and a frame unit memory corresponding to the unit of the processing of the noise reduction circuit.

* * * * *